(12) United States Patent
Ishikawa et al.

(10) Patent No.: US 10,188,344 B2
(45) Date of Patent: Jan. 29, 2019

(54) OPTIMUM ADMINISTRATION FORM PROVIDING SYSTEM FOR MAGNETIC DRUG

(71) Applicants: IHI CORPORATION, Tokyo (JP); Yoshihiro Ishikawa, Tokyo (JP)

(72) Inventors: Yoshihiro Ishikawa, Tokyo (JP); Haruki Eguchi, Tokyo (JP)

(73) Assignees: IHI Corporation, Tokyo (JP); Yoshihiro Ishikawa, Tokyo (JP)

( * ) Notice: Subject to any disclaimer, the term of this patent is extended or adjusted under 35 U.S.C. 154(b) by 517 days.

(21) Appl. No.: 14/758,305

(22) PCT Filed: Dec. 25, 2013

(86) PCT No.: PCT/JP2013/084712
§ 371 (c)(1),
(2) Date: Jun. 29, 2015

(87) PCT Pub. No.: WO2014/104116
PCT Pub. Date: Jul. 3, 2014

(65) Prior Publication Data
US 2015/0351684 A1 Dec. 10, 2015

(30) Foreign Application Priority Data
Dec. 27, 2012 (JP) ................................ 2012-285824

(51) Int. Cl.
*A61B 5/00* (2006.01)
*A61K 41/00* (2006.01)
(Continued)

(52) U.S. Cl.
CPC .......... *A61B 5/4848* (2013.01); *A61B 5/4839* (2013.01); *A61K 41/00* (2013.01);
(Continued)

(58) Field of Classification Search
None
See application file for complete search history.

(56) References Cited

U.S. PATENT DOCUMENTS 7,505,807 B1 * 3/2009 Kucharczyk ....... A61B 5/14525
600/411
8,954,131 B2 * 2/2015 Weaver .................... A61B 5/05
324/300

(Continued)

FOREIGN PATENT DOCUMENTS

JP  2007-297290 A    11/2007
WO  2006/098192 A1    9/2006

(Continued)

OTHER PUBLICATIONS

International Search Report and Written Opinion dated Apr. 1, 2014 corresponding to International Application No. PCT/JP2013/084712.

*Primary Examiner* — Katherine Fernandez
*Assistant Examiner* — Yi-Shan Yang
(74) *Attorney, Agent, or Firm* — Brundidge & Stanger, P.C.

(57) ABSTRACT

A system capable of designing an optimum administration form of a magnetic drug is provided. The system determines first information about an side-effect-related organ on which a magnetic drug produces a side effect, based on equipment analysis information after administering the magnetic drug; further determines second information about a drug-efficacy-related organ in which drug efficacy of the magnetic drug should be demonstrated; evaluates the administration form of the magnetic drug based on the first information and the second information; corrects the administration form of the magnetic drug based on an evaluation result; and outputs information of the corrected administration form.

5 Claims, 2 Drawing Sheets

(51) Int. Cl.
    *A61M 37/00*     (2006.01)
    *A61N 2/00*     (2006.01)
    *G06F 19/00*     (2018.01)
    *A61B 5/055*     (2006.01)
    *A61B 6/03*     (2006.01)
    *A61M 5/20*     (2006.01)

(52) U.S. Cl.
    CPC ............... *A61M 37/00* (2013.01); *A61N 2/00* (2013.01); *G06F 19/00* (2013.01); *A61B 5/055* (2013.01); *A61B 6/032* (2013.01); *A61M 5/20* (2013.01); *A61M 2037/0007* (2013.01)

(56) References Cited

U.S. PATENT DOCUMENTS

| | | | | |
|---|---|---|---|---|
| 2004/0242676 | A1* | 12/2004 | Alessi | A61K 31/353 514/457 |
| 2008/0140371 | A1* | 6/2008 | Warner | A61B 5/0002 703/11 |
| 2009/0311163 | A1* | 12/2009 | Eguchi | A61K 31/282 423/413 |

FOREIGN PATENT DOCUMENTS

| | | |
|---|---|---|
| WO | 2008/001851 A1 | 1/2008 |
| WO | 2008/011851 A1 | 1/2008 |

\* cited by examiner

OPTIMUM ADMINISTRATION FORM PROVIDING SYSTEM FOR MAGNETIC DRUG

CROSS-REFERENCE

This application is a National Stage filing under 35 U.S.C. 371 of PCT Application No. PCT/JP2013/084712, filed Dec. 25, 2013, which claims the benefit of Japanese Patent Application No. 2012-285824, filed Dec. 27, 2012, the entire disclosures of which are incorporated herein by reference.

TECHNICAL FIELD

The present disclosure relates to a system for, for example, designing and setting an optimum administration form for a magnetic drug and providing it to medical personnel.

BACKGROUND ART

A type of drugs called "magnetic drugs" has been conventionally known. This magnetic drug is a drug whose drug element is made to have a magnetic property. A system capable of intensively treating an affected site can be realized by administering a magnetic drug and then applying a magnetic field to a target region such as the affected site and guiding the magnetic drug to the target region.

An example of an administration form of the magnetic drug is a form in which, for example, iron oxide as a magnetic element is micellized together with a drug element and all these elements are made to have the magnetic property. However, the magnetic drug of this form has a problem of losing its magnetic property of the drug as micelles are destroyed due to the influence of metabolism after administration into a body, and the magnetic element breaks away from the drug element.

On the other hand, a self-magnetic drug developed by inventors of the present application does not use the magnetic element separately from the drug, but uses a drug element which itself has the magnetic property. Specifically speaking, the drug element itself is made to have the magnetic property by realizing a form in which the directions of spin electric charges are oriented in one direction within molecules, by applying a molecule designing method of, for example, adding side chains to the molecules of the drug element and forming cross-links between the side chains (WO2008/001851).

This type of self-magnetic drug has various drug efficacies and the inventors of the present application have realized a metal-salen complex having advantageous effects as an anti-cancer drug as one of such drug efficacies (the above-mentioned publication). As the anti-cancer drug itself is given an attribute of the magnetic property, it becomes possible to intensively guide the anti-cancer drug to cancer tissues. On the other hand, an anti-cancer drug treatment regarding which an influence of the anti-cancer drug on areas other than the cancer tissues is reduced and side effects are mitigated can be realized.

CITATION LIST

Patent Literature

[PTL 1] WO2008/001851

SUMMARY OF THE DISCLOSURE

Problems to be Solved by the Disclosure

The use of a high dose of the anti-cancer drug at once might be desired in order to effectively treat a cancer, but such use would cause a significant influence of side effects. So, a conventional anti-cancer drug treatment adopts a treatment form in which 1 to 3 weeks are set as "1 course" and the anti-cancer drug is used in 2 to 8 courses; and after 1 course, a rest period of about 1 to 3 weeks is provided and then the next course is conducted. Specifically speaking, the anti-cancer drug treatment requires a comparatively long period of time, during which a patient experiences severe mental and physical pains and suffering. In fact, the cancer tissues often acquire a metabolic function against the anti-cancer drug, so that the anti-cancer drug becomes no longer effective. Therefore, the conventional anti-cancer drug treatment does not work sufficiently to enhance a patient survival ratio.

On the other hand, the magnetic drug, particularly the self-magnetic drug, can be retained intensively at an affected site, so that the drug efficacy can be expected while reducing the side effects. However, an effective administration form of the magnetic drug has not been established yet and the magnetic drug has not been effectively utilized.

In order to solve the above-described problems, it is an object of the present disclosure to provide a system capable of realizing a treatment method, treatment form, and so on that are useful for effective utilization of the magnetic drug by, for example, designing and setting an optimum administration form of the magnetic drug for each patient and presenting it to medical personnel.

Means for Solving the Problems

In order to achieve the above-described object, the present disclosure provides an optimum administration form providing system for a magnetic drug, the system including: a first determination means that determines first information about a side-effect-related organ on which the magnetic drug produces a side effect, based on equipment analysis information after administering the magnetic drug; a second determination means that determines second information about a drug-efficacy-related organ in which drug efficacy of the magnetic drug should be demonstrated; an evaluation means that evaluates an administration form of the magnetic drug based on the first information and the second information; a correction means that corrects the administration form of the magnetic drug based on the evaluation result; and an output means that outputs information of the corrected administration form.

This system can set the optimum administration form for the magnetic drug by: determining the first information about the side-effect-related organ on which the magnetic drug produces the side effect, based on the equipment analysis information relating the magnetic drug experimentally administered into a body; further determining the second information about the drug-efficacy-related organ in which the drug efficacy of the magnetic drug should be demonstrated; and then modifying the administration form of the experimentally administered magnetic drug based on the first information and the second information.

Advantageous Effects of Disclosure

According to the present disclosure, it is possible to provide a system capable of achieving a treatment based on effective utilization of the magnetic drug by, for example, designing and setting the optimum administration form of the magnetic drug for each patient and presenting it to the medical personnel.

MODE FOR CARRYING OUT THE DISCLOSURE

Figure 1:
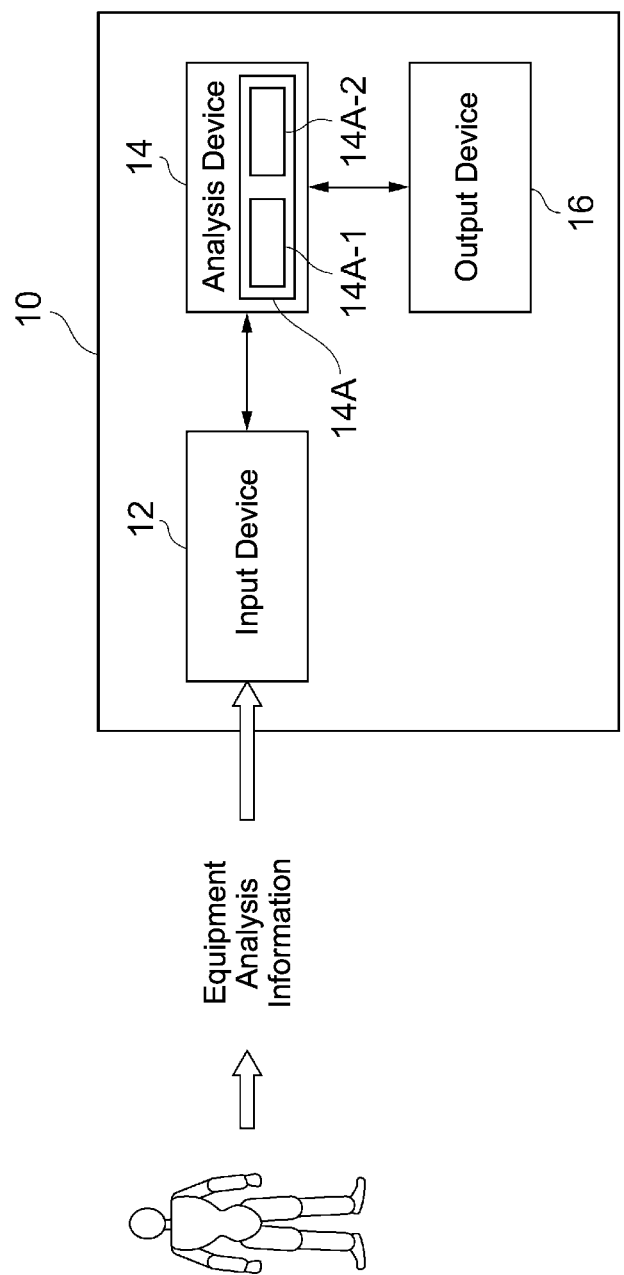
FIG. 1 is a block diagram of an embodiment of an optimum administration form providing system for a magnetic drug according to the present disclosure.

Next, an embodiment of the present disclosure will be explained. An optimum magnetic drug administration form providing system (hereinafter sometimes simply referred to as the "system") 10 according to the present disclosure is implemented by computer hardware as illustrated in FIG. 1. This system 10 includes: an input device 12 for receiving equipment analysis information based on experimental, tentative, or preliminary administration of a magnetic drug to humans or animals from an equipment analysis device as input data; an analysis device 14 for analyzing input information; and an output device 16 for outputting analysis results. The input device 12 may receive the input data from the equipment analysis device via a network or receive the input data via a medium such as a disk or a flash memory.

Any equipment analysis device may be used as long as it can acquire internal body image information such as MRI and X-ray CT. As the magnetic drug, a self-magnetic drug whose molecules of a drug element themselves have the magnetic property is preferred. Particularly, a self-magnetic drug having an anti-cancer effect is preferred in order to enjoy advantageous effects of the present disclosure. The magnetic drug (magnetic substance) can be a contrast agent for the MRI because of its magnetic property. The MRI can output distribution information of the magnetic drug inside the body as image information according to high or low magnetic strength based on differences in a concentration of the magnetic drug. On the other hand, information about, for example, the form and volume of organs such as a liver and kidneys can be obtained by the X-ray CT.

The analysis device 14 includes an arithmetic unit such as a CPU, an MPU, and an image processing chip, a main memory, and a storage unit for storing data programs. The analysis device 14 implements an analysis engine 14A for analysis processing. The analysis engine 14A is achieved by the arithmetic unit executing programs based on analysis data. The arithmetic unit reads necessary data and programs for the analysis processing from the storage unit such as hard disks and records them in the main memory. The analysis engine 14A includes a first engine 14A-1 for analyzing a distribution status of the magnetic drug in the body and a second engine 14A-2 for designing and setting an optimum administration form of the magnetic drug based on the analysis result of the first engine.

Data supplied from the input device 12 to the analysis device 14 includes image data of organs and tissues inside the body and image data showing the distribution status of the magnetic drug as gray-scaled images. Then, detailed information about administration of the magnetic drug is supplied by a system administrator to the input device. The details about the administration include the name of the magnetic drug, attributes of the magnetic drug such as the drug efficacy, an administration concentration of the magnetic drug, a dose of the magnetic drug, attributes relating to the administration such as an administration type (such as intravenous injection or oral administration), attributes relating to patients such as their age, sex, body weight, medical history, and race, and attributes relating to pathology such as a disease name and clinical diagnosis results (for example, types and amounts of cancer markers and other clinical test results). The input data are stored and recorded in the storage unit of the analysis device 14.

A doctor firstly determines the experimental, tentative, or preliminary administration form based on these attributes and administers the magnetic drug to a patient. The terms such as "experimental" used herein means that the magnetic drug is administered to the patient experimentally, tentatively, or preliminary before a real treatment in order to decide the optimum administration form of the magnetic drug. The administration form of the magnetic drug includes the dose of the magnetic drug, dosage such as the administration concentration, the administration method (such as intravenous injection or oral administration), and usage (the number of times of administration per day). The word "optimum" means that it is optimum for the treatment and prevention of the patient's pathosis.

The system 10 obtains image information of the patient (whole body) after the elapse of a specified period of time after administering the magnetic drug to the patient from the MRI and X-ray CT via the input device 12. The acquisition of the image information before the administration of the magnetic drug by the system 10 is preferred in order to extract characteristic values of the image information from differences in the image data before and after the administration of the magnetic drug. Incidentally, when the magnetic drug is administered by means of intravenous injection (including a case of infusion), the specified period of time is, for example, from about 30 minutes to 3 hours. When the magnetic drug is administered by means of oral administration, the specified period of time is, for example, from about half a day to one day.

Figure 2:
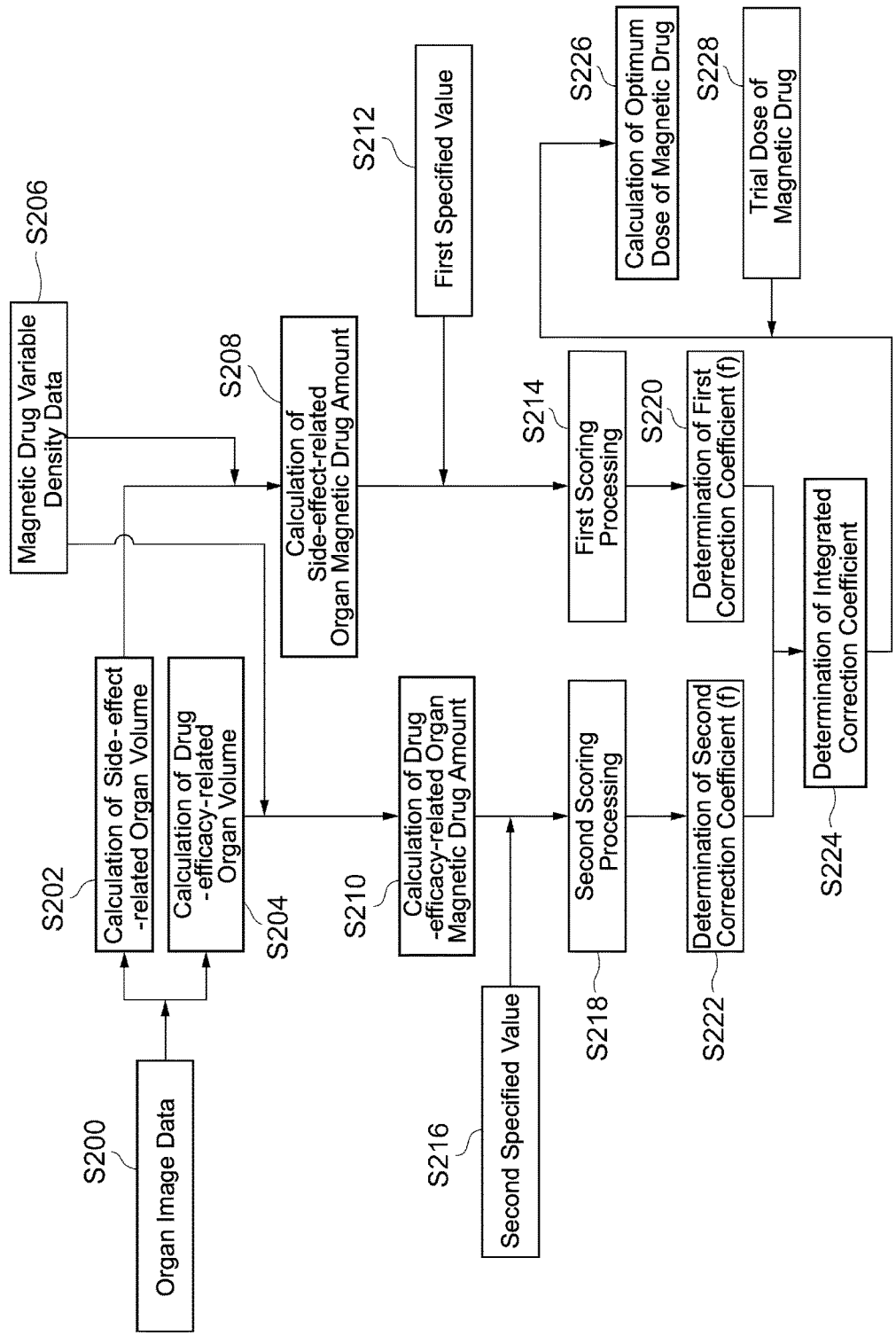
FIG. 2 is a functional block diagram of the optimum administration form providing system for the magnetic drug.

Next, processing of the analysis engine 14A will be explained with reference to FIG. 2. The first engine 14A-1 of the analysis engine 14A corresponds to steps S200 to S210 in FIG. 2 and the second engine 14A-2 corresponds to steps S212 to S228 in FIG. 2. The first engine 14A-1 analyzes the distribution status of the magnetic drug in the body and the second engine 14A-2 determines the optimum administration form of the magnetic drug based on the analysis result.

The first engine 14A-1 distinguishes X-ray CT image data (S200) by each organ or tissue, analyses the image data of these organs and tissues, and extracts a characteristic (volume) of each organ or tissue. As a result, the organ on which attention should be focused can be selected or designated. For example, when therapeutic effects of a specified magnetic drug (metal [iron] salen complex) on a brain tumor (meningioma) are to be expected, the entire brain, partial tissues of, for example, a cerebrum and a cerebellum, or membrane regions such as arachnoidea and meninges can be selected as drug efficacy judgment target organs.

The first engine 14A-1 classifies organs (tissues) into side-effect-related organs related to side effects of the magnetic drug and drug-efficacy-related organs related to drug efficacy of the magnetic drug. This classification is executed based on input information from the administrator. Representative examples of the side-effect-related organs are metabolism-related organs such as a liver and excretion-related organs such as kidneys. When a concentration of the magnetic drug in these side-effect-related organs is high, it means that the side effects of the magnetic drug tend to be easily produced due to insufficient metabolic function and excretion function. The expression "related to side effects" means, for example, to have an influence on the size of the side effects.

On the other hand, a drug-efficacy-related organ is an organ that is a target of treatment with the magnetic drug, for example, an organ where the seat of cancer is located. The first engine 14A-1 finds the side-effect-related organ and the drug-efficacy-related organ according to inputs from the administrator and, in addition, finds the correspondence relationship between the magnetic drug and the side-effect and drug-efficacy-related organs based on a database. The database may exist in the storage unit within the analysis device 14 or in a system separate from the analysis device 14. The first engine 14A-1 calculates the volume of the side-effect-related organ (S202) and the volume of the drug-efficacy-related organ (S204) from the X-ray CT organ image data.

Furthermore, the first engine 14A-1: calculates a magnetic drug concentration from magnetic drug variable density data (S206) of each organ and tissue, which are obtained from the MRI; and multiplies the relevant concentration by the volume of the side-effect-related organ and the drug-efficacy-related organ, thereby calculating a magnetic drug amount of the side-effect-related organ (S208) and calculating the magnetic drug amount of the drug-efficacy-related organ (S210). The magnetic drug amount of the side-effect-related organ corresponds to an example of first information in the claims and the magnetic drug amount of the drug-efficacy-related organ corresponds to an example of second information in the claims. The processing executed by the first engine 14A-1 for calculating the magnetic drug amount of the side-effect-related organ (S208) corresponds to an example of a first determination means in the claims and the processing executed by the first engine 14A-1 for calculating the magnetic drug amount of the drug-efficacy-related organ (S210) corresponds to an example of a second determination means in the claims.

Next, the second engine 14A-2 evaluates each of the side-effect-related organ and the drug-efficacy-related organ with respect to the amount of the magnetic drug. Now, when performing the evaluation, reduction of the side effects of the magnetic drug will be prioritized. This is because, even if the magnetic drug concentration in the whole body is low after administering the magnetic drug, the magnetic drug concentration can be increased intensively in a region of the affected site by applying a magnetic field to the region where the affected site exists, after administering the magnetic drug. In a stage of experimental administration of the magnetic drug, the magnetic field should not be applied to the affected site in order to analyze the influence of the magnetic drug on the whole body. Incidentally, in a second stage of the experimental administration of the magnetic drug, it is possible to continue the analysis by applying the magnetic field to the affected site.

Firstly, the second engine 14A-2 executes: first scoring processing (S214) for comparing an actual magnetic drug amount in the side-effect-related organ with a first specified value (S212); and second scoring processing (S218) for comparing an actual magnetic drug amount in the drug-efficacy-related organ with a second specified value (S216). The first specified value and the second specified value are respectively registered in the database in advance. These specified values are determined according to, for example, sex, body weight, age, the type of disease, the type of the magnetic drug, the dose of the magnetic drug, and an administration method. The specified value is an optimum value of the magnetic drug amount after the elapse of a specified period of time after administration of the magnetic drug when the administration to healthy individuals is assumed.

The second engine 14A-2 determines a score with respect to the side-effect-related organ, for example, as described below.

When the amount of the magnetic drug in the side-effect-related organ after the elapse of the aforementioned specified period of time after experimental administration of the magnetic drug (hereinafter referred to as the "magnetic drug amount") is almost equal to the specified value, the score is "0."

When the magnetic drug amount is much less than the specified value, the score is "+2."

When the magnetic drug amount is less than the specified value, the score is "+1."

When the magnetic drug amount is much more than the specified value, the score is "−2."

When the magnetic drug amount is more than the specified value, the score "−1."

Whether the magnetic drug amount is "much more (or less)" or "more (or less) than" the specified value can be decided as doctors or medical institutions consider proper based on their experiences and knowledge.

When a plurality of side-effect-related organs are set, the second engine 14A-2 calculates the score of each of the plurality of side-effect-related organs, adds these scores to finds an average value, and sets this average value as the score of the side-effect-related organs. A larger negative value of the score of the side-effect-related organs (the related organs) indicates that they tend to have stronger side effects.

Next, the scoring processing executed by the second engine 14A-2 on the drug-efficacy-related organ (the related organ) will be explained.

When the magnetic drug amount is almost equal to the specified value, the score is "0."

When the magnetic drug amount is much more than the specified value, the score is "−2."

When the magnetic drug amount is more than specified value, the score is "−1."

When the magnetic drug amount is much less than the specified value, the score is "+2."

When the magnetic drug amount is less than the specified value, the score is "+1."

When a plurality of drug-efficacy-related organs are set, the second engine 14A-2 calculates the score of each of the plurality of drug-efficacy-related organs, adds these scores to finds an average value, and sets this average value as the score of the drug-efficacy-related organs. A larger negative value of the score of the drug-efficacy-related organs (the related organs) indicates that the drug amount for the drug-efficacy-related organs is sufficient.

When the score of the side-effect-related organ is negative, it is better to reduce the dose. The larger the negative absolute value is, the more a reduction width may be expanded. When the score of the side-effect-related organ is positive, an increase of the dose can be considered. The larger the positive absolute value is, the more an increase width may be expanded.

When the score of the drug-efficacy-related organ is negative, it is better to limit the dose. The larger the negative absolute value is, the more a limitation width may be expanded. When the score of the drug-efficacy-related organ is positive, an increase of the dose can be considered. The larger the positive absolute value is, the more the increase width may be expanded.

The second engine 14A-2 determines a first correction coefficient (f) from the score of the side-effect-related organ (S220). This correction coefficient (f) is to correct an initial dose of the magnetic drug and set an optimum magnetic drug amount; and when the score is negative, the correction coefficient (f) is 0<f<1; and as the negative absolute value becomes larger, the value of the correction coefficient is set smaller. When the score is "0," the first correction coefficient (f) is "1." When the first correction coefficient (f) is "1," it indicates from the viewpoint of the side effects that it is unnecessary to correct or change a trial dose of the magnetic drug.

On the other hand, when the score is positive, the first correction coefficient (f) is 1<f; and as the absolute value becomes larger, the value of the first correction coefficient is set larger.

Next, the second engine 14A-2 determines a second correction coefficient (F) from the score of the drug-efficacy-related organ (S222). This correction coefficient (F) means the same as the first correction coefficient (f). When the score is negative, the correction coefficient is 0<F<1; and as the negative absolute value becomes larger, the value of the correction coefficient is set smaller. When the score is "0," the second correction coefficient (F) is "1." When the second correction coefficient (F) is "1," it indicates from the viewpoint of an effective dose of the drug efficacy that it is unnecessary to correct or change the trial dose of the magnetic drug.

On the other hand, when the score is positive, the second correction coefficient (F) is 1<F; and as the absolute value becomes larger, that will increase the value of the second correction coefficient.

Next, the second engine 12A-2 determines an integrated correction coefficient by multiplying the first correction coefficient (f) by the second correction coefficient (F) (S224) and calculates an optimum dose (S226) by multiplying the integrated correction coefficient by the trial dose of the magnetic drug (S228).

This optimum dose has become an optimum value as a result of correcting the initial dose in consideration of the influence of the side effects of the magnetic drug and ingenuity to have the magnetic drug demonstrate the drug efficacy. The integrated correction coefficient is a coefficient for associating the side effects of the magnetic drug with the drug efficacy of the magnetic drug. The output device 16 displays the optimum dose on a display means to the medical personnel.

Incidentally, the processing of S214 and S218 by the second engine 14A-2 corresponds to an evaluation means in the claims and the processing of S220, S222, S224, and S226 correspond to a correction means in the claims.

When the medical personnel obtains the optimum dose of the magnetic drug, an intensive anti-cancer drug administration treatment for administering the optimum dose at once can be realized without dividing the administration of the anti-cancer drug into a plurality of courses in order to reduce the influence of the side effects. Even if the dose of the magnetic drug is a small amount in comparison with a dose of an anti-cancer drug having a nonmagnetic property, it is possible to apply a high concentration of the magnetic drug to the affected site by externally applying a magnetic field to a region of the affected site.

It is stated that the optimum dose is calculated in S226; however, the second engine 14A-2 may execute simulations to optimize every administration form, for example, by changing a magnetic drug administration method, administration intervals, and magnetic drugs. For example, the system can find a magnetic field application form such as intensity of the magnetic field, an application range (such as a location and area) of the magnetic field, and irradiation time of the magnetic field according to the magnetic property based on differences of types and structures of magnetic drugs, according to the volume of affected site tissues, and according to the optimum dose and then report it to the administrator.

The aforementioned embodiment is an example and can be changed as appropriate within the range of a technical idea of the present disclosure. For example, the side-effect-related organ and the drug-efficacy-related organ may change depending on, for example, the type of the magnetic drug and the location of the affected site. For example, when the score of the first scoring processing is "0" and the score of the second scoring processing "0," it is unnecessary to correct the trial dose of the magnetic drug and, therefore, the processing of S220 and subsequent steps may be suspended.

REFERENCE SIGNS LIST

10: optimum administration form providing system for magnetic drug
12: input device
14: analysis device
16: output device
S208: first determination means
S210: second determination means
S214 and S218: evaluation means
S220, S222, S224, and S226: correction means

The invention claimed is:
1. A system to provide a modified administration form for a magnetic drug, the system comprising:
a memory;
a processor configured to;
obtain equipment analysis information including internal body image data after administering the magnetic drug based on an administration form of the magnetic drug, the administration form including a trial dose of the magnetic drug, wherein the magnetic drug comprises a metal salen complex compound for a brain tumor, and the internal body image data includes X-ray CT image data of organs and MRI image data showing a distribution status of the magnetic drug in the organs as a gray-scaled image,
determine a first concentration about a side-effect-related organ on which the magnetic drug produces a side effect, based on the internal body image data by:
determining a first volume value of the side-effect-related organ from X-ray CT image data of the side- effect-related organ, and
calculating the first concentration of the magnetic drug in the side-effect-related organ, wherein the calculating of the first concentration including:
calculating a magnetic drug density data in the side-effect-related organ from an MRl image data, showing a distribution status of the magnetic drug in the side-effect-related organ, and
multiplying the calculated magnetic drug density data in the side-effect-related organ and the first volume value of the side-effect-related organ to obtain the first concentration, determine a second concentration about a drug-efficacy-related organ in which drug efficacy of the magnetic drug by:
  determining a second volume value of the drug-efficacy-related organ from X-ray CT image data of the drug-efficacy-related organ, and
  calculating the second concentration of the magnetic drug in the drug-efficacy-related organ, wherein the calculating of the second concentration including:
    calculating a magnetic drug density data in the drug efficacy-related organ from an MRI image data showing a distribution status of the magnetic drug in the drug-efficacy-related organ, and
    multiplying the calculated magnetic drug density data in the drug-efficacy-related organ and the second volume value of the drug-efficacy-related organ to obtain the second concentration,
evaluate the administration form of the magnetic drug based on the first concentration and the second concentration by scoring the first concentration and the second concentration in accordance with a predetermined threshold value,
determine, based on the evaluation, an integrated correction coefficient that associates a side-effect of the magnetic drug with a drug efficacy of the magnetic drug, the determining of the integrated correction coefficient including prioritizing a reduction of the side effect of the magnetic drug, and
generate the modified administration form of the magnetic drug that reflects the side-effect of the magnetic drug and the drug efficacy of the magnetic drug based on the integrated correction coefficient, wherein the modified administration form includes an a modified dose of the magnetic drug calculated by multiplying the integrated correction coefficient and the trial dose of the magnetic drug; and
an output device that displays the modified administration form.

2. The system according to claim 1, wherein the processor is configured to score the first concentration and the second concentration by;
  assigning a score to the first concentration of the magnetic drug in the side-effect-related organ by comparing the first concentration to a predetermined threshold concentration of the magnetic drug in the side-effect-related organ, and
  assigning a score to the second concentration of the magnetic drug in the drug-efficacy-related organ by comparing the second concentration to a predetermined threshold concentration of the magnetic drug in the drug-efficacy- related organ.

3. The system according to claim 2,
wherein the processor is configured to
  determine the integrated correction coefficient based on the scoring, the determination of the integrated correction coefficient comprising:
  determining a first correction coefficient (f) from the score of the first concentration of the magnetic drug in the side-effect-related organ,
  determining a second correction coefficient (F) from the score of the second concentration of the magnetic drug in the drug-efficacy-related organ, and
  determining the integrated correction coefficient by multiplying the first correction coefficient (f) and the second correction coefficient (F).

4. The system according to claim 1,
wherein the magnetic drug is an anti-cancer drug and the metal of the metal salen complex compound is an iron.

5. The system according to claim 1, wherein the equipment analysis information further comprises internal body image data before the administering the magnetic drug, and extracted differences between the internal body image data before and after the administering the magnetic drug.

* * * * *